Mar. 8, 1932. J. W. KALLAY Plant Pat. 10
CLIMBING ROSE
Filed March 5, 1931
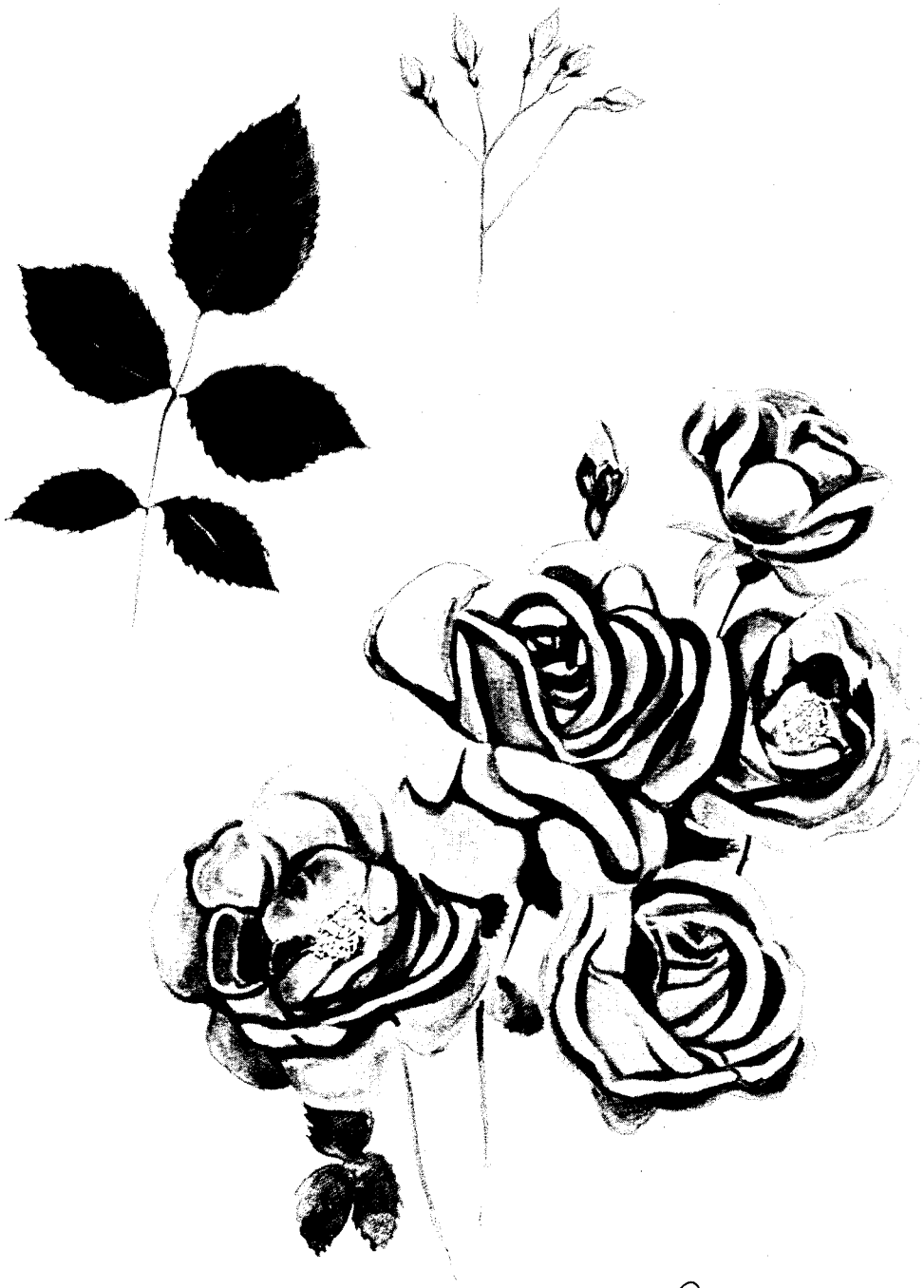
Joseph W. Kallay
INVENTOR
BY Robert Robb
ATTORNEYS Patented Mar. 8, 1932

Plant Pat. 10

UNITED STATES PATENT OFFICE

JOSEPH W. KALLAY, OF PAINESVILLE, OHIO, ASSIGNOR TO JACKSON & PERKINS COMPANY, OF NEWARK, NEW YORK, A CORPORATION OF NEW YORK

CLIMBING ROSE

Application filed March 5, 1931. Serial No. 520,434.

The present invention appertains to a novel and distinct variety of climbing rose, characterized as to novelty by its ever blooming feature, heretofore unknown in hardy climbers.

An ever blooming climber possessing the brilliance of color, so well exemplified by the well known Paul's Scarlet Climber, has long been the aim of rose propagators. This objective has now been achieved by the present origination which is the result of crossing the two known varieties, Paul's Scarlet Climber and Gruss an Teplitz.

It may be remarked that the former of these varieties, it is well known, is a climber whose flower, while odorless, is a most vivid scarlet, having large, open cluster heads, with anywhere from five to fifteen blooms on strong stems. It is a profuse bloomer and a vigorous growing climber but lacking the main desideratum, speaking with reference to the ever blooming characteristic.

On the other hand, the Gruss an Teplitz is a vigorous, upright growing bush marked by the abundance of dark foliage and profuse and continuous blooming throughout the season. The flowers upon this variety come in clusters, each perfect in form, deep crimson or dark, velvety scarlet in color, and intensely fragrant.

The desirable characteristics of both of the above mentioned plants I have now obtained in my present origination which has been duly propagated to determine the persistence of its characteristics. Insofar as the color of the flower is concerned, it is a scarlet crimson with darker shading, deeper than Paul's Scarlet Climber but lighter than the Gruss an Teplitz. It blooms in clusters quite like Paul's Scarlet Climber and its foliage resembles that of said climber with respect to form and size. However, unlike the climber aforesaid, the flower has a fragrance all its own, and in this respect it somewhat resembles Gruss an Teplitz. The wood is green in color, similar also to Paul's Scarlet Climber and its climbing characteristic is like the Paul's.

The most marked improvement over existing types of climbing roses, however, resides in the ever blooming characteristic.

It may be also mentioned that this new variety has very few thorns, not nearly as many as Paul's Scarlet Climber, and it follows its other parent rather in respect to this particular feature.

The accompanying illustration gives as nearly as possible a true representation or reproduction of the blooms which are found upon this new variety of climbing rose.

The specifications herein set forth the general characteristic of the rose, yet it is understood they may vary slightly due to cultivation and environment.

What is claimed as new is:

The climbing rose herein shown and described, characterized by its ever-blooming habit.

In testimony whereof I affix my signature.

JOSEPH W. KALLAY.